United States Patent
Xu et al.

(10) Patent No.: US 7,700,816 B2
(45) Date of Patent: Apr. 20, 2010

(54) CATALYTIC CONVERSION OF OXYGENATES TO OLEFINS

(75) Inventors: Teng Xu, Houston, TX (US); Tan-Jen Chen, Kingwood, TX (US); Neeraj Sangar, League City, TX (US); John Di Yi Ou, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 843 days.

(21) Appl. No.: 11/484,305

(22) Filed: Jul. 11, 2006

(65) Prior Publication Data

US 2007/0043250 A1 Feb. 22, 2007

Related U.S. Application Data

(60) Provisional application No. 60/709,221, filed on Aug. 18, 2005.

(51) Int. Cl.
C07C 1/00 (2006.01)
B01J 29/00 (2006.01)
B01J 27/182 (2006.01)

(52) U.S. Cl. ............ 585/640; 502/66; 502/71; 502/74; 502/76; 502/77; 502/78; 502/79; 502/214; 502/524; 502/525

(58) Field of Classification Search ............ 585/640; 502/66, 71, 74, 77, 78, 79, 214, 524, 525
See application file for complete search history.

(56) References Cited

U.S. PATENT DOCUMENTS

| | | | |
|---|---|---|---|
| 4,025,575 A | 5/1977 | Chang et al. | |
| 4,062,905 A | 12/1977 | Chang et al. | |
| 4,083,889 A | 4/1978 | Caesar et al. | |
| 4,179,409 A | 12/1979 | Gladrow et al. | |
| 4,247,731 A * | 1/1981 | Wunder et al. | 585/640 |
| 4,310,440 A | 1/1982 | Wilson et al. | |
| 4,440,871 A | 4/1984 | Lok et al. | |
| 4,471,150 A | 9/1984 | Wu | |
| 4,499,327 A | 2/1985 | Kaiser | |
| 4,677,242 A | 6/1987 | Kaiser | |
| 4,677,243 A | 6/1987 | Kaiser | |
| 4,873,390 A | 10/1989 | Lewis et al. | |
| 5,095,163 A | 3/1992 | Barger | |
| 5,367,100 A | 11/1994 | Gongwei et al. | |
| 5,714,662 A | 2/1998 | Vora et al. | |
| 6,166,282 A | 12/2000 | Miller | |
| 2002/0171633 A1 | 11/2002 | Brinjes | |
| 2003/0176752 A1 | 9/2003 | Levin et al. | |
| 2003/0176753 A1 | 9/2003 | Levin et al. | |
| 2003/0181325 A1 | 9/2003 | Ou et al. | |
| 2003/0187314 A1 | 10/2003 | Wang et al. | |
| 2004/0030213 A1 | 2/2004 | Levin et al. | |

FOREIGN PATENT DOCUMENTS

| | | |
|---|---|---|
| EP | 0 083 160 | 7/1983 |
| EP | 0 318 808 | 6/1987 |
| EP | 0 532 034 | 3/1993 |
| WO | WO 98/29370 | 7/1998 |
| WO | WO 2000/69796 | 11/2000 |
| WO | WO 2006/023095 | 3/2006 |
| WO | WO 2006/038949 | 4/2006 |

* cited by examiner

Primary Examiner—In Suk Bullock
(74) Attorney, Agent, or Firm—Kevin M. Faulkner; David M. Weisberg

(57) ABSTRACT

An oxygenate conversion catalyst useful in the conversion of oxygenates such as methanol to olefinic products may be improved by the use of a catalyst combination based on a molecular sieve in combination with a co-catalyst comprising a mixed metal oxide composition which has oxidation/reduction functionality under the conditions of the conversion. This metal oxide co-catalyst component will comprise a mixed oxide of one or more, preferably at least two, transition metals, usually of Series 4, 5 or 6 of the Periodic Table, with the metals of Series 4 being preferred, as an essential component of the mixed oxide composition. The preferred transition metals are those of Groups 5, especially titanium and vanadium, Group 6, especially chromium or molybdenum, Group 7, especially manganese and Group 8, especially cobalt or nickel. Other metal oxides may also be present. The preferred molecular sieve components in these catalysts are the high silica zeolites and the SAPOs, especially the small pore SAPOs (8-membered rings), such as SAPO-34. These catalyst combinations exhibit reduced coke selectivity have the potential of achieving extended catalyst life. In addition, these catalysts have the capability of selectively converting the hydrogen produced during the conversion to liquid products, mainly water, reducing the demand on reactor volume and product handling.

16 Claims, No Drawings

CATALYTIC CONVERSION OF OXYGENATES TO OLEFINS

CROSS REFERENCE TO RELATED APPLICATIONS

This application claims the benefit of Provisional Application No. 60/709,221 filed Aug. 18, 2005, the disclosure of which is fully incorporated herein by reference.

FIELD OF THE INVENTION

The present invention relates to a process for the conversion of oxygenates such as methanol and lower alkanols to product stream including olefins; it also relates to catalytic compositions for this process.

BACKGROUND OF THE INVENTION

Olefins have been conventionally produced from petroleum feedstocks by a number of processes including catalytic cracking of heavy oil feedstocks as well as by steam cracking of light paraffins such as ethane. Light olefins such as ethylene and propylene are important commodity petrochemicals useful in a variety of processes for making plastics and other chemical compounds.

Oxygenates, especially the lower alcohols, may be converted into light olefin(s). There are a number of technologies available for producing oxygenates including fermentation of biomass, reaction of synthesis gas derived from natural gas, petroleum liquids or carbonaceous materials including coal, recycled plastics, municipal waste or other organic materials. Generally, the production of synthesis gas involves a combustion reaction of natural gas, mostly methane, and an oxygen source into hydrogen, carbon monoxide and/or carbon dioxide. Other known syngas production processes include steam reforming, autothermal reforming and combinations of these processes. Methanol, the preferred alcohol for light olefin production, is typically synthesized from the catalytic reaction of syngas (hydrogen, carbon monoxide and/or carbon dioxide) in the presence of a heterogeneous catalyst. For example, in one synthesis process methanol is produced using a copper/zinc oxide catalyst in a water-cooled tubular methanol reactor.

Oxygenates, especially methanol may be converted into hydrocarbons, especially light olefins such as ethylene and propylene, by what are essentially dehydration and dehydrogenation reactions. A number of processes for converting a methanol feedstock into olefin(s), primarily ethylene and/or propylene, have been operated or proposed in the past. In general, these processes are conducted by contacting the feedstock with a molecular sieve catalyst under conditions of elevated temperature. An early example of such a process was the Methanol-to-Gasoline Process devised by Mobil Oil Corporation and implemented commercially at Motunui, New Zealand, using a fixed bed of zeolite catalyst with methanol feed produced from natural gas.

Olefins, which find wide utility as petrochemical feedstocks, may also be produced from oxygenates such as methanol. Processes for converting methanol and other oxygenates to product streams containing major amounts of olefins by reaction over zeolite catalysts are described, for example, in U.S. Pat. No. 4,025,575; U.S. Pat. No. 4,083,889 and U.S. Pat. No. 5,367,100 where the catalyst is a ZSM-5 zeolite and U.S. Pat. No. 4,471,150 and EP 0083 160 where the catalyst is an 8-membered ring zeolite such as ZSM-34. U.S. Pat. No. 4,062,905 discloses the conversion of methanol and other oxygenates to ethylene and propylene using crystalline aluminosilicate zeolites, for example Zeolite T, ZK5, erionite and chabazite; U.S. Pat. No. 4,310,440 describes the production of light olefin(s) from an alcohol using a crystalline aluminophosphate, often generically designated as $AlPO_4$.

Some of the most useful molecular sieves for converting methanol to olefin(s) are silicoaluminophosphate molecular sieves. Silicoaluminophosphate (SAPO) molecular sieves contain a three-dimensional microporous crystalline framework structure of $[SiO_4]$, $[AlO_4]$ and $[PO_4]$ corner sharing tetrahedral units and may be synthesized by the hydrothermal crystallization of a reaction mixture of silicon-, aluminum- and phosphorus-sources and at least one templating agent, for example, as described in U.S. Pat. No. 4,440,871. The use of SAPO molecular sieve catalysts for converting feedstocks such as methanol into olefin(s) is disclosed in U.S. Pat. No. 4,499,327, U.S. Pat. No. 4,677,242, U.S. Pat. No. 4,677,243, U.S. Pat. No. 4,873,390, U.S. Pat. No. 5,095,163, U.S. Pat. No. 5,714,662 and U.S. Pat. No. 6,166,282.

Typically, the molecular sieve crystals are formed into finished catalysts which have improved durability in the commercial conversion processes. These molecular sieve catalyst compositions are formed by combining the molecular sieve and a matrix e.g. an inorganic oxide such as alumina, titania, zirconia, silica or silica-alumina with a binder, e.g. clay, to form a coherent, stable, attrition-resistant composite of the sieve, matrix material and binder. Usually, the binder and matrix materials typically only serve to provide desired physical characteristics to the catalyst composition, and have little to no effect on conversion and selectivity of the molecular sieve.

Recently, attention has been given to the use of various materials in combination with the molecular sieve component and the matrix/binder materials to improve the performance of the catalyst in one respect or another. US 2002/0171633, for example, discloses the use of a catalyst composition comprising a SAPO, preferably SAPO-34, in combination with a calcined metal oxide such as magnesium oxide which exhibits certain acetone conversion characteristics. This combination is said to result in longer catalyst life when used in oxygenate conversion processes as well as having improved selectivity for propylene production, with reduced amounts relatively of ethane and propane.

US 2003/0176752 describes an oxygenate conversion catalyst based on a combination of a molecular sieve such as SAPO-34 with a metal oxide of Group 4 (IUPAC Periodic Table) such as zirconia or hafnia either alone or in combination with an oxide of a metal of Group 2 such as an oxide of calcium, magnesium, strontium or barium. This combination also, is said to result in extended catalyst life as well as in enhanced olefin yield and improved propylene selectivity. A similar process is described in US 2003/0176753 which describes an oxygenate conversion catalyst with similar advantages, based on a combination of a molecular sieve such as SAPO-34 with an oxide of a metal selected from Group 3 (IUPAC Periodic Table), the lanthanide or actinide series where the oxide is characterized by a defined value of carbon dioxide uptake.

US 2004/0030213 describes an oxygenate conversion catalyst based on a combination of a molecular sieve such as SAPO-34 and an oxide of a metal of Group 3, the lanthanide series and the actinide series. Examples of such oxides include lanthanum oxide, yttrium oxide, scandium oxide, cerium oxide, praseodymium oxide, neodymium oxide, samarium oxide and thorium oxide. This catalytic combination is reported to result in similar advantages when used in methanol conversion reactions and, in addition, results in a reduction in the amounts of undesirable by-products such as aldehydes and ketones, especially acetaldehyde. It is also stated that the higher density of these catalyst compositions is believed to improve operability in the overall conversion process carried out in fluid cracking type equipment because the denser catalyst particles are retained to a greater extent within the unit, whether in the reactor of its associated regenerator, resulting in lower catalyst losses. WO 98/29370 also discloses the conversion of oxygenates to olefins over a small pore non-zeolitic molecular sieve containing an oxide of a lanthanide metal, an actinide metal, scandium, yttrium, a Group 4 metal, a Group 5 metal or combinations of these.

Another approach to the problems of achieving improved selectivity to the desired light olefins such as ethylene and propylene as well as extended catalyst life by reducing coke formation, that is, of reducing coke selectivity, is described in US 2003/0187314 which discloses the use in methanol conversion of a catalyst based on a molecular sieve such as SAPO-34 which has been treated with a solution of a metal alkyl organometallic compound in a non-proton donating solvent. Suitable metal alkyls are reported to include dimethyl zinc and exemplary solvents include light paraffins such as heptane.

These approaches have been notable but improved catalyst life as well as improved olefin yield and selectivity to the desired ethylene and propylene products is still desired.

The catalyst life is related to the coke selectivity of the catalyst since accumulation of coke on the catalyst although largely removed during regeneration will eventually result in deactivation, if only as a result of the increased exposure to hydrothermal deactivation during the regeneration. In addition, high coke laydown on the catalyst increases the demand for regeneration capacity and the regenerator is one of the most expensive items of equipment in a typical commercial methanol conversion unit. Thus, reductions in coke selectivity are highly prized.

A problem that is related to coke selectivity is that of hydrogen production: hydrogen is produced in proportion to the coke since the coke itself is formed by removal of hydrogen and oxygen components of the feedstock. The typical product stream from methanol conversion includes about 0.1 weight percent hydrogen, an amount which is low on a weight basis but corresponds to a relatively high volume (about 0.7 percent volume basis) since hydrogen is the lightest of all molecules. The volume occupied by the hydrogen in the product stream therefore requires the reactor and related equipment to be larger than they otherwise would be. Reductions in the volume of hydrogen in the conversion products therefore represents a substantial desideratum.

SUMMARY OF THE INVENTION

It has now been found that the coke selectivity of an oxygenate conversion catalyst may be improved by the use of a catalyst combination based on a molecular sieve in combination with a mixed metal oxide which has oxidation/reduction functionality under the conditions of the conversion. The conversion catalyst will include a molecular sieve component, typically with a matrix component and a binder and a solid, mixed metal oxide which exhibits this oxidation/reduction capability under the conditions which are encountered in the conversion reactions. This metal oxide co-catalyst component will comprise a mixed oxide of a transition metal, usually of Series 4, 5 or 6 of the Periodic Table, with the metals of Series 4 being preferred as the essential component of the oxide composition. In preferred catalyst compositions, at least two oxides of transition metals from Series 4 and 5 will be present; in most cases it suffices to use transition metals from Series 4 and 5, with preference given to transition metals of Groups 5, especially titanium and vanadium, Group 6, especially chromium or molybdenum, and Group 8, especially iron, cobalt or nickel with cobalt or nickel being preferred. Other metal oxides may be used in these mixed oxide compositions, including oxides of metals of Group 4 including zirconium, and Group 2, especially magnesium, calcium or barium. Group 3 (Rare Earth) metal oxides may also be present, for example, scandium oxide, lanthanum oxide, yttrium oxide, as well as oxides of metals from the lanthanide series such as cerium and the related thorium oxide from the actinide series.

The preferred molecular sieve components in these catalysts are the SAPO materials, especially those characterized as having small, medium or large pore sizes, with preference being given to the small pore SAPOs (8-membered rings) including especially SAPO-34.

The mixed metal oxide co-catalytic components may be readily made by the calcination of a mixture of metal oxides containing the requisite metal oxides to form the final mixed oxide material. Such mixed oxides may have various mineral structures including those of various spinels and perovskites.

In the process, a feedstock comprising an oxygenate such as methanol or ethanol is converted to an olefin-containing product stream under conversion conditions in the presence of the catalyst combination comprising a molecular sieve and the mixed metal oxide co-catalyst component having oxidation/reduction functionality under the conditions of the conversion.

These catalyst combinations exhibit reduced coke selectivity as compared to other catalyst combinations of molecular sieves and metal oxides and therefore have the potential of achieving extended catalyst life when used in these conversion processes. In addition, these catalysts have been demonstrated to have the capability, believed to result from the oxidation/reduction functionality, of converting the hydrogen produced during the conversion to liquid products, mainly water, which reduces the demand on reactor volume and therefore enables reductions in equipment costs to be achieved.

DETAILED DESCRIPTION

The present invention relates to a process for converting oxygenate feedstocks such as methanol or ethanol to a product stream containing significant quantities of olefins. As noted above, oxygenate conversion processes of this general type have been previously used commercially and described. In the present process, the conversion of the oxygenate feedstock to the olefins is carried out in the presence of a catalyst which comprises a molecular sieve component and a mixed oxide component including an oxide of a transition metal which exhibits oxidation/reduction functionality under the conditions of the conversion.

Feedstock

The feedstock contains one or more oxygenates, that is, one or more organic compound(s) containing at least one oxygen atom. Typically, the oxygenate in the feedstock is one or more lower alcohols, although other oxygenates such as aldehydes, ketones, ethers, carboxylic acids and organic carbonates may also be used. The preferred oxygenates, especially the alcohols, are aliphatic compounds where the aliphatic moiety has from 1 to 20 carbon atoms, usually from 1 to 10 carbon atoms, and in most cases from 1 to 4 carbon atoms. Alcohols which may be used include lower straight and branched chain aliphatic alcohols and their unsaturated counterparts. Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures of such oxygenated compounds.

The preferred feedstocks are methanol, ethanol, dimethyl ether, diethyl ether or a combination of these lower alcohols and/or ethers, of which methanol and dimethyl ether are preferred with the most preferred feed being methanol.

In the process, the feedstock is converted primarily into one or more olefin(s) although, as described below, other products are also formed. The olefin(s) produced in this way typically have from 2 to 30 carbon atoms, usually 2 to 8 carbon atoms and in most cases 2 to 6 carbon atoms. The 2 to 4 carbons atom olefins are the most preferred products, especially ethylene and/or propylene.

In addition to the oxygenate component, e.g. methanol, the feedstock may contain one or more diluent(s), which may be non-reactive to the feedstock or molecular sieve catalyst composition and are typically used to reduce the concentration of the feedstock. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures of these. The most preferred diluents are water and nitrogen, with water being particularly preferred.

The diluent, for example, water, may be used either in a liquid or a vapor form, or in a mixed phase feed. It may be either added directly to the feedstock entering a reactor or added directly to the reactor, or added with the molecular sieve catalyst composition in a moving bed or fluidized bed operation. Typically, the amount of fresh feedstock fed as a liquid and/or a vapor to the reactor system is in the range of from 0.1 weight percent to about 85 weight percent, such as from about 1 weight percent to about 75 weight percent, more typically from about 5 weight percent to about 65 weight percent based on the total weight of the feedstock including any diluent contained in the feed. The liquid and vapor feedstocks may be the same composition, or may contain varying proportions of the same or different feedstocks with the same or different diluents.

Catalyst

The catalyst characteristically used in the present process contains a molecular sieve component and a mixed oxide component. The molecular sieves which are useful in the conversion of oxygenate feeds to olefins are well known. They typically include zeolites, aluminophosphates (ALPOs), silicoaluminophosphates (SAPOs) and other materials as described below.

Molecular sieves have been classified by the Structure Commission of the International Zeolite Association according to the rules of the IUPAC Commission on Zeolite Nomenclature. According to this classification, framework-type zeolite and zeolite-type molecular sieves, for which a structure has been established, are assigned a three letter code and are described in the *Atlas of Zeolite Framework Types,* 5th edition, Elsevier, London, England (2001). Crystalline molecular sieves all have a 3-dimensional, four-connected framework structure of corner-sharing [TO$_4$] tetrahedra, where T is any tetrahedrally coordinated cation. Molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition,* Volume 137, pages 1-67, Elsevier Science, B. V., Amsterdam, Netherlands (2001).

The small, medium and large pore molecular sieves have from a 4-ring to a 12-ring or greater framework-type. The preferred zeolitic molecular sieves for use in the present process may have 8-, 10- or 12-ring structures and an average pore size in the range of from about 3 Å to 15 Å. The preferred sieves, preferably the silicoaluminophosphate sieves, have 8-rings and an average pore size less than about 5 Å, such as in the range of from 3 Å to about 5 Å, for example from 3 Å to about 4.5 Å, and particularly from 3.5 Å to about 4.2 Å.

The aluminosilicate, aluminophosphate and silicoaluminophosphate molecular sieves have a molecular framework of one, preferably two or more, corner-sharing [TO$_4$] tetrahedral units, more preferably, two or more [SiO$_4$], [AlO$_4$] and/or [PO$_4$] tetrahedral units, and most preferably [SiO$_4$], [AlO$_4$] and [PO$_4$] tetrahedral units. These silicon, aluminum, and phosphorus based molecular sieves and metal containing derivatives thereof have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 (AlPO$_4$), EP-A-0 158 350 (SENAPSO), U.S. Pat. No. 4,973,460 (Li-APSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit [QO$_2$]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference. Other molecular sieves include those described in R. Szostak, *Handbook of Molecular Sieves,* Van Nostrand Reinhold, New York, N.Y. (1992).

The more preferred molecular sieves for use in the present process include aluminophosphate (AlPO) molecular sieves and silicoaluminophosphate (SAPO) molecular sieves and substituted, preferably metal substituted, AlPO and SAPO molecular sieves. The most preferred molecular sieves for use in the present process are the SAPO molecular sieves, and metal substituted SAPO molecular sieves. In one form of these sieves, the metal is an alkali metal of Group 1 of the Periodic Table of Elements, an alkaline earth metal of Group 2 of the Periodic Table of Elements, a rare earth metal of Group 3 of the Periodic Table of Elements, including the lanthanides: lanthanum, cerium, praseodymium, neodymium, samarium, europium, gadolinium, terbium, dysprosium, holmium, erbium, thulium, ytterbium and lutetium; and scandium or yttrium, a transition metal of Groups 4 to 12 of the Periodic Table of Elements, or mixtures of any of these metal species. In one preferred embodiment, the metal is selected from Co, Cr, Cu, Fe, Ga, Ge, Mg, Mn, Ni, Sn, Ti, Zn and Zr, and mixtures of these cations. In another preferred embodiment, these metal atoms discussed above are inserted into the framework of a molecular sieve through a tetrahedral unit, such as [$MeO_2$], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve in its as-synthesized form is represented by the empirical formula, on an anhydrous basis mR:($M_xAl_yP_z$)$O_2$, as described in many of the U.S. patents mentioned above, where R represents at least one templating agent, preferably an organic templating agent; m is the number of moles of R per mole of ($M_xAl_yP_z$)$O_2$ and has a value from 0 to 1, preferably 0 to 0.5, and most preferably from 0 to 0.3; x, y, and z represent the mole fraction of Al, P and M as tetrahedral oxides, where M is a metal selected from one of Groups 1, 2, 3, 4, 5, 6, 7, 8, 9, 10, 11, 12, 13, 14 and Lanthanide's of the Periodic Table of Elements, preferably M is selected from one of the group consisting of Si, Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01. In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and AlPO molecular sieves useful in the present process include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, AlPO-5, AlPO-11, AlPO-18, AlPO-31, AlPO-34, AlPO-36, AlPO-37, AlPO-46, and metal containing molecular sieves derived from these materials. Of these, particularly useful molecular sieves are one or a combination of SAPO-18, SAPO-34, SAPO-35, SAPO-44, SAPO-56, AlPO-18 and AlPO-34 and their metal containing derivatives, such as one or a combination of SAPO-18, SAPO-34, AlPO-34 and AlPO-18, and their metal containing derivatives, and especially one or a combination of SAPO-34 and AlPO-18, and their metal containing derivatives.

In an embodiment, the molecular sieve is an intergrowth material having two or more distinct crystalline phases within one molecular sieve composition. In particular, intergrowth molecular sieves are described in the U.S. patent application Ser. No. 09/924,016 filed Aug. 7, 2001 and International Publication No. WO 98/15496 published Apr. 16, 1998, to which reference is made for a description of these materials. For example, SAPO-18, AlPO-18 and RUW-18 have an AEI framework-type, and SAPO-34 has a CHA framework-type. Thus the molecular sieve may comprise at least one intergrowth phase of AEI and CHA framework-types, especially where the ratio of CHA framework-type to AEI framework-type, as determined by the DIFFaX method disclosed in U.S. patent application Ser. No. 09/924,106 filed Aug. 7, 2001, is greater than 1:1.

The aluminosilicate zeolites are also useful methanol conversion catalysts, as described in U.S. Pat. No. 4,471,150, especially the medium (or intermediate) pore size zeolites and the small pore size zeolites, although the large pore size zeolites such as faujasite, mordenite (MOR), offretite, zeolite L, zeolite X, zeolite Y, USY, ZSM-4, ZSM-20 may also be useful. The medium pores size zeolites are characterized by the possession of a ring structure comprising ten-membered rings of oxygen atoms; zeolites of this type include ZSM-5 (MFI), ZSM-11 (MEL), ZSM-12 (MTW) and the relatively more constrained medium pore zeolites such as ferrierite (FER), ZSM-22, ZSM-23 (MTT), ZSM-35 (which possesses both ten- and eight-membered rings). Newer classes of the medium pore size zeolites include the MWW family of zeolites, a family which includes zeolites PSH 3, MCM-22, MCM-49, MCM-56, SSZ-25, ERB-1 and ITQ-1. The small pore size zeolites may be used to advantage in the present process, these materials possess an eight-membered ring of oxygen atoms and are exemplified by zeolites having the CHA, ERI, LTA, LEV and AEI framework structures. In general, highly siliceous zeolites are preferred and particularly zeolites with silica:alumina molar ratios above 20, such as above 50:1, for example above 100:1, and typically above. 250:1.

Particularly preferred zeolite catalysts are the high silica, wherein the silica:alumina molar ratio is from 100 to infinity (no alumina present), zeolites with an CHA, faulted CHA, AEI or CHA/AEI intergrown framework types disclosed in U.S. Patent Application Publication No. 2003/0176751, published Sep. 18, 2003, U.S. Patent Application Publication No. 2005/0154244, published Jul. 14, 2005, U.S. patent application Ser. No. 11/017,091, filed Dec. 20, 2004, and U.S. patent application Ser. No. 11/017,092, filed Dec. 20, 2004, the entire contents of which are incorporated herein by reference.

The molecular sieve component may be synthesized by known methods such as those described in the references cited above. Generally, these molecular sieves are synthesized by the hydrothermal crystallization of one or more of a source of aluminum, a source of phosphorus (if present in the sieve), a source of silicon and a templating agent, such as a nitrogen containing organic compound. Typically, for the SAPOs a combination of sources of silicon, aluminum and phosphorus, optionally with one or more templating agents, is placed in a sealed pressure vessel, optionally lined with an inert plastic such as polytetrafluoroethylene, and heated, under a crystallization pressure and temperature, until a crystalline material is formed, and then recovered by filtration, centrifugation and/or decanting. More detailed descriptions of molecular sieve synthesis techniques applicable to the preferred SAPO sieve components may be found in the references cited above relating to SAPOs and in U.S. Patent Application Publication Nos. 2004/0030213 A1; 2003/0176752 A1 and 2003/0176753 A1, to which reference is made for a description of such synthesis techniques.

Mixed Metal Oxide Co-Catalyst

The characteristic catalysts used in the present process include, in addition to the molecular sieve component, a mixed metal oxide component as a co-catalyst which exhibits oxidation/reduction capability under the conditions which are encountered in the conversion of the oxygenate(s) to the olefin product. This metal oxide co-catalyst component will comprise at least one oxide of a transition metal, preferably two, usually of Series 4, 5 or 6 of the Periodic Table, with preference given to transition metals of Groups 5 (especially vanadium), Group 6 (especially chromium or molybdenum), Group 7 (especially manganese) and Group 8 (especially iron, cobalt or nickel). Other metal oxides may however be used in these mixed oxide compositions, including oxides of metals of Group 4 including zirconium, Group 1 (Alkali Metals) such as sodium, potassium, cesium, Group 2 (Alkaline Earth metals), especially magnesium, calcium or barium. Oxides of Rare Earth metals (scandium, yttrium, lanthanum, as well as of from the lanthanide series, e.g. cerium), may also be present as well as the related thorium oxide from the actinide series.

The notable feature of this mixed metal oxide component is that it is capable of exhibiting oxidation/reduction functionality under the conditions used in the conversion. This behavior is marked by first, the existence of multiple valence states in the metal, a characteristic of many transition metals although the present mixed oxide co-catalysts are required to be capable of existing in at least two valence states under the conditions which are encountered in the overall course of the conversion process. The conditions prevailing at any one point in the process, taken in the temporal or locational sense, will vary and the transition metal may be stable in one particular valence state at the conditions then or there prevailing; however, at the conditions encountered at a different time or location in the overall process, the metal should be capable of passing into an alternative valence state at some times and/or places while the process is taking place. The conditions under which the process takes place are described below in terms of process parameters such as temperature, pressure, catalyst/feed ratio (WHSV); the conditions under which the co-catalyst will be required to exhibit the requisite redox functionality will therefore be difficult to define in a single parameter or even a simple combination of parameters; validation of acceptability can therefore be determined indirectly by the Selective Hydrogen Combustion test described below in which the co-catalyst is tested in a blend with the primary conversion catalyst for methanol-to-olefin conversion.

Another characteristic of the present catalyst compositions is that the mixed transition metal oxide component is a selective hydrogen combustion (SHC) catalyst. As noted above, one of the problems encountered in the oxygenate-to-olefin conversion process is that large volumes of hydrogen are produced along with the desired olefins and this may impose a process limitation if existing equipment is unable to handle the hydrogen or, if new equipment is being designed, it may have to be larger than would otherwise be necessary in order to handle the hydrogen, so imposing additional capital costs. The present catalyst systems are capable of promoting the combustion of the hydrogen which is formed in the conversion reactions to water which, being liquid at normal temperatures and pressures, occupies less volume than the hydrogen from which it is formed, so that the volume of the product stream is reduced. Although combustion catalysts are well known, for example, platinum, which would be capable of promoting combustion of hydrogen and hydrocarbons in the presence of oxygen, it is immediately obvious that the combustion which is desired in the present process should be selective for the hydrogen, that is, the catalyst should selectively promote the combustion of the hydrogen while being inactive—or, at least, relatively inactive—for promoting the combustion of the hydrocarbons which are formed by the conversion of the oxygenates. The present catalyst system has shown itself to possess this capability in being active for hydrogen combustion while being relatively inactive for hydrocarbon combustion. Compared to other simple and mixed metal oxides which may be used in combination with molecular sieves in the conversion process, for example, lanthanum/zirconium oxide, the preferred co-catalysts which are acceptable according to the present invention reduce the volume of hydrogen produced in the process by a factor of at least 2 and preferably at least 3, as compared to a baseline comparison catalyst such as $La_2O_3$—$ZrO_2$ oxide. In favorable cases, the present co-catalysts may have a hydrogen volume reduction factor of at least 5 or even higher, for example, at least 6, e.g. in the range of 6 to 7.

The transition metal component of the mixed oxide co-catalyst is one or more metals of Groups 4, 5, 6, 7 or 8 of the Periodic Table (IUPAC Table format as shown, for instance, in www.iupac.org/reports/periodic_table/ and CRC *Handbook of Chemistry and Physics,* 78th Edition, CRC Press, Boca Raton, Fla. (1997)) and for preference the transition metal is an element of Series 4, 5 or 6 of the Periodic Table. Transition metals conforming to this specification include vanadium, chromium, manganese, iron, cobalt, nickel, molybdenum, hafnium, tungsten, and cerium. The preferred transition metals are vanadium, chromium, molybdenum, manganese, iron, cobalt and/or nickel. While other transition metals may exhibit multiple valence states in general terms, or may act as hydrogen combustion catalysts, they do not generally exhibit the oxidation/reduction functionality under the conditions encountered during the present process, as described above, or the desired selectivity to hydrogen combustion over hydrocarbon combustion. Thus, zirconium and lanthanum, while possessing multiple valence states, do not exhibit oxidation/reduction functionality under the conditions prevailing in the conversion process and for this reason, may be used in the present mixed metal oxide co-catalysts only in combination with one or more oxides of metals which do possess the required functionality and hydrogen selectivity. Zirconium, lanthanum and other metals may therefore be used in the form of their oxides in these mixed oxide compositions when a metal having the requisite redox functionality is present. Thus, metals of Group 1 (alkali metals), including sodium, potassium and cesium; Group 2, especially the alkaline earth metals magnesium, calcium or barium, may be used together with the transition metal component as well as the rare earth metals including scandium, yttrium and lanthanum and the 14 lanthanides: cerium, praseodymium, neodymium, promethium, samarium, europium, gadolinium, terbium, dysprosium, holmium, erbium, thulium, ytterbium and lutetium as well as the related metal thorium from the actinide series. Of these, scandium, yttrium, lanthanum, cerium, thorium are likely to be preferred for economic reasons.

The mixed metal oxide co-catalytic component may be readily synthesized by mixing together the selected metal oxides or their precursors and calcining the mixture together to form the mixed oxide composition. It is preferred that the metal oxide whether it is of the transition metal or another metal should be made from a metal oxide precursor, such as a metal salt, for example, a halide, nitrate sulfate or acetate or a compound that is converted to the corresponding metal oxide during calcination, for example, an oxychloride, nitrate, hydroxide, carbonate or an alkoxide, for example zirconium propoxide. A preferred source of zirconia when used in addition to the required transition metal component is hydrated zirconia (a material comprising zirconium atoms covalently linked to other zirconium atoms via bridging oxygen atoms, with available hydroxyl groups). The metal oxides or their selected precursors are mixed together and then calcined at high temperature, typically at least 500° C. (about 930° F.) and usually at least 600° C. (about 1110° F.) or even higher, for example, 750° C. (about 1380° F.) for a period of time typically of at least 1 hour, usually at least 2 hours. If metal oxide precursors are used, it is normally preferred to increase the temperature gradually to final desired calcination temperature in order to allow time for gaseous by-products from the calcination treatment, e.g. steam, nitrogen oxides, carbon dioxide, to be desorbed from the mixture.

The proportions of the various metal oxides in the final calcined, mixed oxide composition is not normally important and may be determined by empirical procedures based on overall catalytic performance. The resultant mixed oxides may have various mineral structures including those of various spinels and perovskites, depending on the oxides used in the synthesis and their relative amounts.

Catalyst Formulation

The mixed catalyst system comprising the molecular sieve and the mixed oxide coo-catalytic component may be used as separate components of the final catalytic system or, more preferably, they may be incorporated into a single particle catalyst. If the metal oxide co-catalyst is used separately from the molecular sieve component, that is, as an additive catalyst, both the molecular sieve component and the mixed oxide co-catalyst may be formulated with a matrix material and/or binder to form a finished catalyst with the requisite handling properties, e.g. attrition resistance. If the molecular sieve component and the metal oxide co-catalyst component are to be used in a single particle catalyst, they may both be formulated into the finished catalyst composition with the same matrix and/or binder. For this purpose, conventional matrixing and formulation methods and materials may be used, for example, spray drying a slurry of the catalytic component(s) with the selected matrix material(s) and/or binder(s). Suitable matrix materials include the inorganic oxides alumina, silica, silica-alumina, titania, zirconia and the like. Binders such as clays may be used alone or with a matrixing oxide such as alumina or silica. The matrix or binder may be supplied in the form of a precursor such as aluminum chlorhydrate which is converted to the final oxide form when the catalyst formulation is calcined to give it its final properties as a finished catalyst. A more extended description of matrix and binder materials and the manner in which the catalyst components may be formulated into the finished catalyst, with specific examples, is given in US 2003/0176752 A1 and US 2003/0176753 A1, to which reference is made for such details.

Normally, the amount of the molecular sieve component of a catalyst system will be from 5 to 80 weight percent of the total composition, usually from 20 to 65 weight percent; the mixed metal oxide co-catalyst will normally comprise from 5 to 50 weight percent of the weight of the molecular sieve component (omitting binder); in most cases, it will be from 10 to 30 weight percent of the molecular sieve component (omitting binder 0. Because the function of the co-catalyst is to extend the life of the prime conversion component (the sieve) and to reduce the volume of hydrogen by-product, these relatively smaller amounts will normally be found to be effective although resort may be made to empiricism to determine the optimum relative amount for use in the process when operated under particular selected conditions.

In one embodiment, prior to being used to convert oxygenate to olefins, the catalyst is pretreated with dimethyl ether, a $C_2$-$C_4$ aldehyde composition and/or a $C_4$-$C_7$ olefin composition to form an integrated hydrocarbon co-catalyst within the porous framework of the intergrown molecular sieve. Desirably, the pretreatment is conducted at a temperature of at least 10° C., such as at least 25° C., for example at least 50° C., higher than the temperature used for the oxygenate reaction zone and is arranged to produce at least 0.1 wt %, such as at least 1 wt %, for example at least about 5 wt % of the integrated hydrocarbon co-catalyst, based on total weight of the molecular sieve. Such preliminary treating to increase the carbon content of the molecular sieve is known as "pre-pooling" and is further described in U.S. application Ser. Nos. 10/712,668, 10/712,952 and 10/712,953 all of which were filed Nov. 12, 2003 (now US Published Applications Nos. US 2005/01011815, US 2005/01011816 and US 2005/01011817, respectively), to which reference is made for a full description of the pre-pooling treatment.

Process

The present oxygenate conversion process can be conducted over a wide range of temperatures, such as in the range of from about 200° C. to about 1000° C. Typical temperature ranges include, for example, from about 250° C. to about 800° C., with narrower more typical ranges of about 250° C. to about 750° C., about 300° C. to about 650° C., from about 350° C. to about 600° C. and particularly from about 350° C. to about 550° C. Similarly, the process can be conducted over a wide range of pressures including autogenous pressure. Typically the partial pressure of the feedstock exclusive of any diluent therein employed in the process is in the range of from about 0.1 kPaa to about 5 MPaa, such as from about 5 kPaa to about 1 MPaa, and conveniently from about 20 kPaa to about 500 kPaa.

The weight hourly space velocity (WHSV), defined as the total weight of feedstock excluding any diluents per hour per weight of molecular sieve in the catalyst composition, typically ranges from about 1 $hr^{-1}$ to about 5000 $hr^{-1}$, such as from about 2 $hr^{-1}$ to about 3000 $hr^{-1}$, for example from about 5 $hr^{-1}$ to about 1500 $hr^{-1}$, and conveniently from about 10 $hr^{-1}$ to about 1000 $hr^{-1}$. In one embodiment, the WHSV is greater than 20 $hr^{-1}$ and, where feedstock contains methanol and/or dimethyl ether, is in the range of from about 20 $hr^{-1}$ to about 300 $hr^{-1}$.

The process of the invention is conveniently conducted as a fixed bed process, or, for preference, as a fluidized bed process (including a turbulent bed process), such as a continuous fluidized bed process, and particularly a continuous high velocity fluidized bed process. The conversion process can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and Fluidization Engineering, D. Kunii and O. Levenspiel, Robert E. Krieger Publishing Company, New York, N.Y. 1977, to which reference is made for a description of such reactor types. The process is conveniently conducted as a fixed bed process, or more typically as a fluidized bed process (including a turbulent bed process), such as a continuous fluidized bed process, and particularly a continuous high velocity fluidized bed process. When conducted in a fluidized bed, the superficial gas velocity (SGV) of the feedstock including diluent and reaction products within the reactor system, and particularly within a riser reactor(s), is at least 0.1 meter per second (m/sec), such as greater than 0.5 m/sec, such as greater than 1 m/sec, for example greater than 2 m/sec, conveniently greater than 3 m/sec, and typically greater than 4 m/sec, as described in U.S. Pat. No. 6,552,240, to which reference is made for a description of suitable riser operational conditions.

The preferred fluidized reactor types are riser reactors generally described in Riser Reactor, Fluidization and Fluid-Particle Systems, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), to which reference is made for a description of suitable reactor configurations.

The fluidized catalyst operation regimes, fluidized bed or high velocity fluidized bed normally include a reactor system, a regeneration system and a recovery system. The reactor system will usually include a fluid bed reactor system having a first reaction zone within one or more riser reactor(s) and a second reaction zone within at least one disengaging vessel, typically comprising one or more cyclones. In one form, the riser reactor(s) and disengaging vessel are contained within a single reactor vessel. Fresh oxygenate feedstock, optionally with one or more diluent(s), is fed to the riser reactor(s) to which the conversion catalyst composition (or a coked catalyst composition) is also introduced. Heat is normally supplied by the catalyst coming from the regenerator after its oxidative regeneration. Prior to being introduced to the riser reactor(s), the conversion catalyst composition (or coked catalyst) may be contacted with a liquid, preferably water or methanol, and/or a gas, for example, an inert gas such as nitrogen.

The amount of fresh feedstock fed as a liquid and/or a vapor to the reactor system is typically in the range of from 0.1 weight percent to about 85 weight percent, such as from about 1 weight percent to about 75 weight percent, more typically from about 5 weight percent to about 65 weight percent of the total weight of feedstock plus any diluent. The liquid and vapor feedstocks may be the same composition, or may contain varying proportions of the same or different feedstocks with the same or different diluents.

The feedstock entering the reactor system is converted, partially or fully, in the reactor zone into a gaseous effluent that enters the disengaging vessel along with the coked catalyst. Normally, cyclone(s) within the disengaging vessel carry out the required separation of coked catalyst from the gaseous effluent containing the desired olefin product. Although cyclones are preferred, gravity or inertial effects within the disengaging vessel can also be used to separate the catalyst composition from the gaseous effluent. Other methods for separating the catalyst composition from the gaseous effluent include the use of plates, caps, elbows, and the like.

The disengager(s) are normally followed by a stripping zone, typically in a lower portion of the disengaging vessel. In the stripping zone the coked catalyst composition is contacted with a gas, preferably one or a combination of steam, methane, carbon dioxide, carbon monoxide, hydrogen, or an inert gas such as argon, preferably steam, to recover entrained hydrocarbons from the coked catalyst which is then passed to the regeneration system. The gaseous effluent is withdrawn from the disengaging system and is passed through a recovery system.

The coked catalyst withdrawn from the disengaging vessel is introduced to the regenerator where the coked catalyst is regenerated by oxidative removal of the coke by contacted with a regeneration medium which is a gas containing oxygen, under regeneration conditions of temperature, pressure and residence time. Examples of suitable regeneration media include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. Under the conditions prevailing in the regenerator, the coke is burned from the coked catalyst, preferably to a level less than 0.5 weight percent (based on the total weight of the coked molecular sieve catalyst entering the regeneration system). The regeneration temperature may typically be in the range of from about 200° C. to about 1500° C., such as from about 300° C. to about 1000° C., for example from about 450° C. to about 750° C., and conveniently from about 550° C. to 700° C. The regeneration pressure may be in the range of from about 15 psia (103 kPaa) to about 500 psia (3448 kPaa), such as from about 20 psia (138 kPaa) to about 250 psia (1724 kPaa), including from about 25 psia (172kPaa) to about 150 psia (1034 kPaa), and conveniently from about 30 psia (207 kPaa) to about 60 psia (414 kPaa).

The average residence time of the catalyst in the regenerator may be in the range of from about one minute to several hours, such as from about one minute to 100 minutes, and the volume of oxygen in the regeneration gas may typically be in the range of from about 0.01 mole percent to about 5 mole percent based on the total volume of the gas.

The burning of coke in the regeneration step is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated catalyst composition from the regeneration system and passing it through a catalyst cooler to form a cooled regenerated catalyst composition. Other methods for operating a regeneration system are disclosed in U.S. Pat. No. 6,290,916 (controlling moisture).

The regenerated catalyst withdrawn from the regeneration system, preferably taken through a catalyst cooler, and returned to the riser reactor(s). A carrier, such as an inert gas, feedstock vapor, steam or the like, may be used, semi-continuously or continuously, to facilitate the introduction of the regenerated catalyst composition to the reactor system. By controlling the flow of the regenerated catalyst composition or cooled regenerated catalyst composition from the regeneration system to the reactor system, the optimum level of coke on the molecular sieve catalyst composition entering the reactor is maintained. Coke levels on the catalyst, after regeneration, are in the range of from 0.01 to about 15 weight percent, with successively narrower ranges likely to be encountered of from about 0.1 to about 10 weight percent, from about 0.2 to about 5 weight percent, and from about 0.3 to about 2 weight percent based on the weight of the molecular sieve.

Product recovery systems may be conventional in type; there are many known recovery systems, techniques and sequences that are useful in separating olefin(s) and purifying olefin(s) from the gaseous effluent. Recovery systems as well as other features of the oxygenate conversion process and process equipment are described briefly in U.S. Patent Applications Publication Nos. 2003/0176752 A1 and 2003/0176753 A1, to which reference is made for further details of the process and of suitable process equipment, including the recovery systems.

Using the present catalyst compositions for the conversion of the oxygenate feedstocks, the amount of olefin(s) produced based on the total weight of hydrocarbon produced is greater than 50 weight percent, greater than 60 weight percent in most cases, e.g. greater than 70 weight percent, and in favorable cases, greater than 80 weight percent. The amounts of ethylene and/or propylene produced is, moreover, typically greater than 40 weight percent, typically greater than 50 weight percent, for example greater than 65 weight percent, and preferably greater than 78 weight percent based on the total weight of hydrocarbon product produced. Typically, the amount ethylene produced (same basis), is greater than 20 weight percent, e.g. greater than 30 or 40 weight percent. In addition, the amount of propylene produced (same basis) is typically greater than 20 weight percent, e.g. greater than 25 or 30 weight percent, and in favorable cases, greater than 35 weight percent.

Using the present conversion catalysts with methanol and dimethylether feedstocks for ethylene and propylene and production, it may be possible to reduce the production of ethane and propane by 10% or more, e.g. 20% or more, for example, greater than 30%, and particularly in the range of from about 30% to 40% compared to a similar catalyst composition at the same conversion conditions but without the mixed metal oxide co-catalyst component. The volume of hydrogen by-product coming out of the conversion may be reduced by at least 50 volume percent, in favorable cases, by over 60 volume percent, enabling equipment to be used more efficiently for the desired olefin products.

In addition to the desired olefin product(s), a number of additional products, by-products and/or contaminants are normally produced. Examples of contaminants and by-products include generally polar compounds such as water, alcohols, carboxylic acids, ethers, carbon oxides, sulfur compounds such as hydrogen sulfide, carbonyl sulfides and mercaptans, ammonia and other nitrogen compounds, arsine, phosphine and chlorides. Other contaminants or by-products include hydrogen and hydrocarbons such as acetylene, methyl acetylene, propadiene, butadiene and butyne. Typically, in converting one or more oxygenates to $C_2$-$C_3$ olefin(s), a minor amount hydrocarbons, particularly olefin(s), having 4 or more carbon atoms is also produced. The amount of $C_{4+}$ hydrocarbons is normally less than 20 weight percent, and may be less than 10 weight percent, for example less than 5 weight percent, and less than 2 weight percent in favorable cases (based on the total weight of the effluent gas withdrawn from the process, excluding water).

The preferred light olefin products from the process are high purity prime olefin(s) products that contain a single carbon number olefin in an amount greater than 80 percent, which may be greater than 90 weight percent, or higher, for example, greater than 95 or even as high as about 99 weight percent, in favorable cases (based on the total weight of the olefin products).

The following Examples illustrate the preparation of the mixed oxide components of the catalyst and their formulation into a complete catalyst composition, followed by catalytic evaluation.

Example 1

Preparation of $ZrOCl_2$/$ZrO_2$ Colloid (Denoted as ZrZr) Supported $Mg_{0.25}Na_zMnO_x$ Spinel Zirconium oxychloride octahydrate ($ZrOCl_2.8H_2O$, 1.4505 g.) was added to zirconia (2.775 g) in the form of $ZrO_2$ colloid (100 nm, 20 wt %) and the mixture well mixed for 2 hours. To this mixture was added 1.8 g of a mixed magnesium/manganese oxide $Mg_{0.25}Na_zMnO_x$ from above to form a paste which was then well mixed to form a paste. The paste was then dried by ramping up the temperature at 1° C./min to 120° C., and holding at this temperature for 2 hours. The dried material was then calcined by ramping up temperature to 560° C. and hold for 2 hours. The catalyst thus prepared was designated as CAT 328.

Example 2

Preparation of $Ce(NO_3)_3$/$ZrO_2$ Colloid (Denoted as CeZr) Supported $Mg_{0.25}NazMnO_x$ Spinel Cerium nitrate hexahydrate, $Ce(NO_3)_3.6H_2O$, (1.26 g.) was added to zirconia (1.79 g.) in the form of $ZrO_2$ colloid (100 nm, 20 wt %) and the mixture well mixed for 2 hours. To the resulting CeZr mixture was added 1.2 g. of a mixed magnesium/manganese oxide, $Mg_{0.25}Na_zMnO_x$ from above to form a paste and the paste was well mixed. The mixture was dried by ramping up the temperature at 1° C./min to 120° C. at which value it was held for 2 hours. The dried mixture was then calcined by ramping up temperature to 560° C. and holding for 2 hours. The catalyst thus prepared was designated as CAT 329.

Example 3

Preparation of $La_{0.2}Ca_{0.8}Mn_{0.54}Co_{0.36}Ti_{0.1}O_3$ Perovskite

Concentrated nitric acid (2.5 ml) was added to approximately 25 ml of anhydrous ethanol in a 100 ml beaker and stirred. Titanium isopropoxide (1.565 g.) was then added and the resulting solution mixed for a few seconds before being added quickly (about 5 seconds) to a solution of concentrated nitric acid in distilled water (2.5 ml acid in approximately 275 ml distilled water) on the stir plate.

To this solution was added lanthanum nitrate hexahydrate, $La(NO_3)_3.6H_2O$ (4.767 g.) as well as calcium nitrate tetrahydrate, $Ca(NO_3)2.4H_2O$, (10.398 g.) and manganese nitrate, $Mn(NO_3)2.xH_2O$, (8.460 g.) and cobalt nitrate hexhydrate, $Co(NO_3)_2.6H_2O$, (5.767 g.). The resulting solution was stirred to dissolve the salts, making care to ensure a clear solution.

Isopropanol (952 g.) was added to a 35% aqueous solution of tetraethylammonium hydroxide (245 g.) in a 2000 ml beaker and mixed for 3 minutes. The solution of mixed lanthanum, calcium, manganese, cobalt nitrates was then added slowly for 1-3 minutes while stirring. The resulting suspension was aged for 1 hour while stirring. The solid particulate product was recovered by centrifuging (30 setting, 2 centrifuge bottles per batch) and washed twice with isopropanol (600 ml.). The product was dried overnight in 10 cm. glazed ceramic bowl, using 1 bowl per batch of about 9 grams of catalyst.

The sample was then ground with mortar and pestle and the ground material calcined in flowing air by heating up at 5° C./min and holding at 800° C. for 2 hours. The catalyst thus prepared is designated as CAT 241.

Example 4

Catalyst Evaluation for MTO

The molecular sieve catalyst (CAT 61F) was a formulated catalyst, comprising 40 weight percent SAPO-34/SAPO-18 intergrowth molecular sieve, 12 weight percent ACH (aluminum chlorhydrol) binder and with the balance (48 weight percent) being clay (matrix material). A sample of this catalyst was intimately mixed with the selected candidate catalyst, e.g., CAT 241, using a mortar and pestle to form a blended catalyst composition. The SAPO catalyst (CAT 61F) and the selected candidate were blended in a weight ratio of 80:20 (61F: Candidate), respectively.

The blended MTO conversion catalyst comprising CAT 61F with the candidate was evaluated for MTO performance with the use of a microflow reactor. Typically, ca. 115 mg of the blended catalyst composition was mixed with 1 g of 100-μm silicon-carbide. The mixture was loaded into the reactor, which is made of 8 mm silicon-steel tubing. The reactor temperature was increased to 475° C. while the catalyst was under He flow (46 ml/min), and held for ca. 30 to 40 min for the temperature to stabilize.

Methanol was introduced into the prepooled (as described above) catalyst at 80 μl/min at 100 WHSV and 25 psig while the effluent was sampled by a 16-loop Valco™ valve. Typically, 9 to 15 samples were analyzed to obtain the weighed average selectivity. The collected effluent samples were analyzed by on-line gas chromatography (Hewlett Packard 6890, Q-column) equipped with a flame ionization detector.

The weighed average yields were calculated based on the formula:

$$x1*y1+(x2-x1)*y2+(x3-x2)*(y2+y3)/2+(x4-x3)*(y3+y4)/2+\ldots$$

where $xi$ and $yi$ are yield and g methanol fed/g sieve, respectively. The WHSV was reported based on the weight of the sieve. Methanol converted at less than ca. 10% conversions were not counted in the calculations. Selectivities were calculated by normalizing the yield data excluding methanol and DME.

Quantification of the extension in catalyst life is determined by the Lifetime Enhancement Index (LEI) as defined by the following equation:

$$LEI = \frac{\text{Lifetime of Catalyst in Combination with Active Metal Oxide}}{\text{Lifetime of Catalyst}}$$

where the lifetime of the catalyst or catalyst composition, in the same process under the same conditions, is the cumulative amount of feedstock processed per gram of catalyst composition until the conversion of feedstock by the catalyst composition falls below some defined level, for example 10%.

TABLE 1

Summary of lifetime enhancement index for CAT 61F with co-catalysts

|  | C1 | C2= | C2o | C3= | C3o | C4s | C5+s | C2+3= | LEI |
|---|---|---|---|---|---|---|---|---|---|
| Control-CAT 61F | 1.62 | 37.71 | 0.30 | 40.42 | 0.89 | 13.14 | 5.93 | 78.12 | 1.0 |
| CAT 61F + CAT 241 | 1.99 | 30.41 | 0.19 | 42.58 | 0.81 | 13.81 | 10.20 | 72.99 | 7.4 |
| CAT 61F + CAT 328 | 2.14 | 32.33 | 0.21 | 42.90 | 0.70 | 13.90 | 7.81 | 75.23 | 4.6 |
| CAT 61F + CAT 329 | 1.95 | 32.18 | 0.21 | 42.81 | 0.74 | 14.04 | 8.07 | 74.99 | 5.3 |

C1, C2=, C2o, C3=, C3o, C4s, C5+s and C2+3= in Table 1 refer, respectively, to methane, ethylene, ethane, propene, propane, butenes and butanes, hydrocarbons that contain five or more than five carbons, ethylene and propene.

Example 5

CAT 61F Control Experiment

The lifetime of CAT 61F catalyst was measured to be 18.3 g methanol converted/g sieve. By definition, the LEI of CAT 61F is one.

Example 6

Catalyst Composition of 61F and CAT 241

The lifetime of the catalyst composition was measured to be 134.9 g methanol converted/g sieve. The LEI for the catalyst composition is 7.4.

Example 7

Catalyst Composition of CAT 61F and CAT 328

The measured lifetime of the catalyst composition is 83.6 g methanol converted/g sieve, and LEI of the composition is 4.6.

Example 8

Catalyst Composition of CAT 61F and CAT 329

The measured lifetime of the catalyst composition is 97.8 g methanol converted/g sieve, and the LEI for the composition is 5.3.

The data shown in Examples 4-7 clearly show that the lifetime of catalyst composition involving a hydrogen combustion catalyst has been significantly increased compared to the formulated SAPO-34/SAPO-18 catalyst (CAT 61F) without a hydrogen combustion co-catalyst.

Example 9

Experimental Details for SHC Tests

In addition to the MTO life tests, the ZrZr and CeZr supported spinel and perovskite catalysts were also tested for their selective hydrogen combustion (SHC) activity. For this purpose, a portion of the original sample of CAT 241 (perovskite) was used; the two spinels were represented by catalysts identified as CAT 164 and CAT 166 which were from different batches than the ones used in the MTO life time studies but made using the identical procedure to that used for CAT 328 and CAT 329, respectively.

In the SHC tests, a commercial ZSM-5 catalyst from W. R. Grace (OlefinsMax™)was used as the base. In the base case run, 0.5 grams of the ZSM-5 catalyst was pelletized, crushed and screened to 30-50 mesh (US Standard) powder. The fresh ZSM-5 catalyst was then physically mixed with silicon carbide (3.0 g., 16-25 mesh), and loaded into a fixed-bed reactor for testing. The catalyst was heated to 540° C. in a helium stream at a flow rate of 105 cc/min at a pressure of 14-27 kPag (2-4 psig). The temperature was allowed to stabilize for 30 minutes prior to the addition of hydrocarbon feed. The feed comprised 0.384 cc/min of 2-methylpentane and 0.025 cc/min of liquid water. Following the introduction of hydrocarbon feed, product samples were collected every 30 seconds for a total time-period of 3.5 minutes using a multi-port, gas-sampling valve. The product was analyzed using a gas chromatograph equipped with flame ionization and pulsed discharge detectors.

In the SHC tests with the supported spinel and perovskite catalysts, 0.5 grams of the catalyst of interest was mixed physically with 0.5 grams of the ZSM-5 catalyst. The feed composition and feed rate were kept the same as the base case. The product was also analyzed similarly as the base case. The difference in the yield of hydrogen compared to the base case provides a measure of the capability of the candidate catalyst to reduce the volume of hydrogen produced in the process. The performance of the supported spinels and perovskite was compared to that of lanthanum zirconia, which has been previously shown to be effective in enhancing the life of SAPO-34 in MTO.

TABLE 2

Hydrogen Combustion Selectivity of Catalysts

| Catalyst | Hydrogen Reduction, % |
|---|---|
| ZSM-5 + 5% $La_2O_3$—$ZrO_2$ | 10 |
| ZSM-5 + ZrZr Spinel (CAT 164) | 61 |
| ZSM-5 + CeZr Spinel (CAT 166) | 58 |
| ZSM-5 + Perovskite (CAT 241) | 69 |

As can be seen from Table 2 above, the supported spinel and perovskite catalysts are much more effective than lanthanum zirconia in reducing the volume of produced hydrogen. The supported spinels and perovskite catalysts showed hydrogen conversion in the range of 50-70%, 5-7 times higher than that of lanthanum zirconia.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

We claim:

1. A process for converting an oxygenate-containing feedstock into one or more olefin(s) in the presence of a molecular sieve catalyst composition comprising a molecular sieve and a mixed metal oxide composition that exhibits oxidation/reduction functionality under the conditions of the conversion, wherein the catalyst composition has a Selective Hydrogen Combustion (SHC) activity of at least 25 percent, and wherein the mixed metal oxide composition has the structure of a spinel or a perovskite.

2. The process of claim 1 in which the oxygenate of the feedstock comprises methanol, ethanol and/or dimethylether.

3. The process of claim 1 in which the mixed metal oxide composition comprises the oxide of at least one transition metal of Series 4, 5 or 6 of the Periodic Table.

4. The process of claim 3 in which the mixed metal oxide composition comprises the oxides of at least two transition metals of Series 4, 5 or 6 of the Periodic Table.

5. The process of claim 3 in which the mixed metal oxide composition comprises an oxide of at least one transition metal of Series 4, Groups 4, 5, 6, 7 or 8 of the Periodic Table.

6. The process of claim 3 in which the mixed metal oxide composition comprises an oxide of at least one of vanadium, chromium, molybdenum, manganese, iron, cobalt and/or nickel.

7. The process of claim 3 in which the mixed metal oxide composition comprises, in addition to the oxide of the transition metal, an oxide of at least one metal of Group 1 or Group 2 of the Periodic Table.

8. The process of claim 3 in which the mixed metal oxide composition comprises zirconia, titania or lanthanum oxide in addition to the oxide of at least one other transition metal of Series 4, 5 or 6 of the Periodic Table.

9. The process of claim 1 in which the catalyst composition has a Selective Hydrogen Combustion (SHC) activity of at least 50 percent.

10. The process of claim 1 in which the molecular sieve comprises a silicophosphoaluminate.

11. The process of claim 1 in which the molecular sieve comprises a silicophosphoaluminate having an 8-membered ring structure.

12. The process of claim 1 in which the molecular sieve comprises SAPO-18, SAPO-34, an intergrowth of SAPO-18 and SAPO-34 or a combination of these.

13. The process of claim 1 in which the molecular sieve comprises a silicate or alumino silicate.

14. The process of claim 13 in which the silicate or aluminosilicate has a CHA and/or an AEI framework structure.

15. The process of claim 14 wherein the silicate or aluminosilicate has a silica to alumina molar ratio greater than 100.

16. The catalyst of claim 1, wherein the transition metals in the spinel are Zr, Ce, or a mixture thereof.

* * * * *